United States Patent [19]

Johnson

[11] Patent Number: 4,650,477
[45] Date of Patent: Mar. 17, 1987

[54] SUCTION DRAINAGE APPARATUS
[75] Inventor: Robert H. Johnson, Sandy, Utah
[73] Assignee: Sorenson Research Co. Inc., Salt Lake City, Utah
[21] Appl. No.: 775,846
[22] Filed: Sep. 13, 1985

Related U.S. Application Data

[63] Continuation of Ser. No. 434,681, Oct. 15, 1982, abandoned.

[51] Int. Cl.$^4$ ............................................. A61M 1/00
[52] U.S. Cl. ................................... 604/321; 604/118; 604/320
[58] Field of Search ................... 141/59; 137/205; 604/118, 119, 317-323, 327, 49

[56] References Cited

U.S. PATENT DOCUMENTS

| 918,117 | 4/1909 | Blackwell | 251/215 |
|---|---|---|---|
| 3,363,626 | 1/1968 | Bidwell et al. | 604/321 |
| 3,363,627 | 1/1968 | Bidwell et al. | 604/321 |
| 3,381,687 | 5/1968 | Anderson et al. | 141/59 |
| 4,289,158 | 9/1981 | Nehring | 137/205 |
| 4,296,748 | 10/1981 | Kurtz et al. | 604/323 |
| 4,396,386 | 8/1983 | Kurtz et al. | 604/319 |
| 4,419,093 | 12/1983 | Deaton | 604/49 |

FOREIGN PATENT DOCUMENTS

| 1069409 | 1/1980 | Canada | 604/49 |
|---|---|---|---|
| 2082071 | 3/1982 | United Kingdom | 604/319 |

OTHER PUBLICATIONS

"Understanding Underwater Chest Drainage", Chesebrough-Ponds Inc., Greenwich, Conn. 06830, 1976.
"University Physics," Sears and Zemansky, Addison-Wesley Publishing Co. Inc., Reading, Mass., 1964, p. 479.

Primary Examiner—C. Fred Rosenbaum
Assistant Examiner—J. L. Kruter
Attorney, Agent, or Firm—Martin L. Katz; Michael J. Roth

[57] ABSTRACT

A suction drainage system for body cavities includes a suction collection container, and a disposable suction control chamber through which an essentially constant level of suction is applied to a body cavity. Drained fluids flow into the suction collection container, into the suction control chamber through an elastomeric check valve which precludes backflow of fluids to the patient. A pressure monitoring tube in the suction control chamber has a lower end communicating with ambient pressure and an upper end communicating with the interior of the suction control chamber. A ball in the tube rises to a level which is proportional to the negative pressure inside the suction control chamber. The suction control chamber can be removably mounted to the collection container.

32 Claims, 6 Drawing Figures

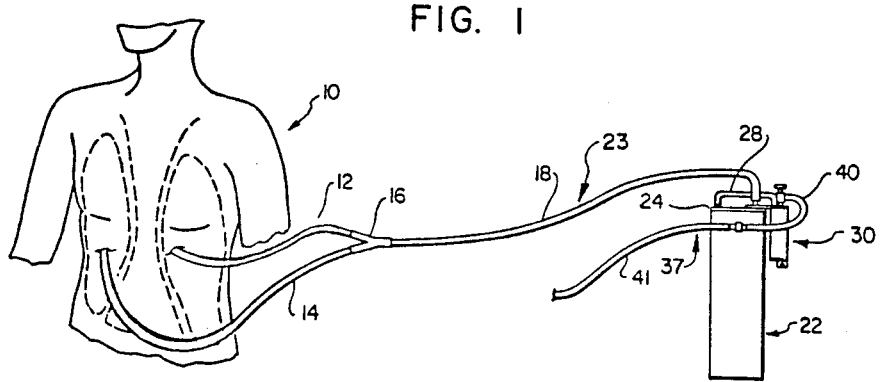
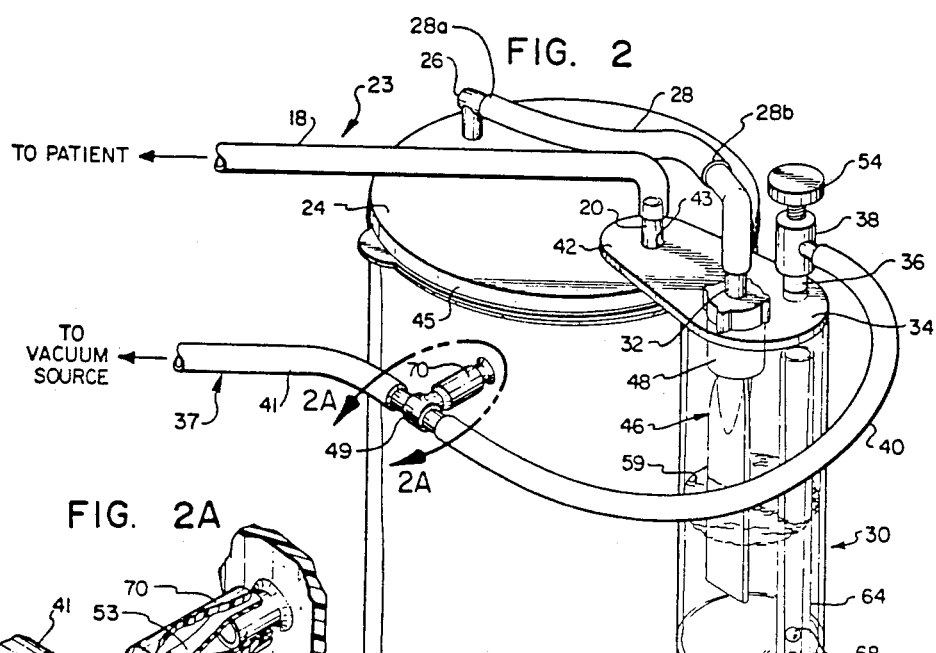
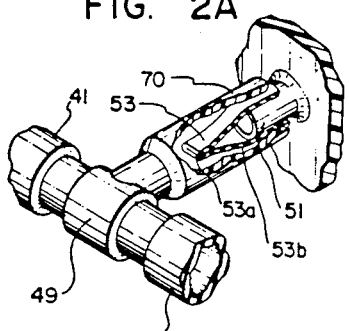

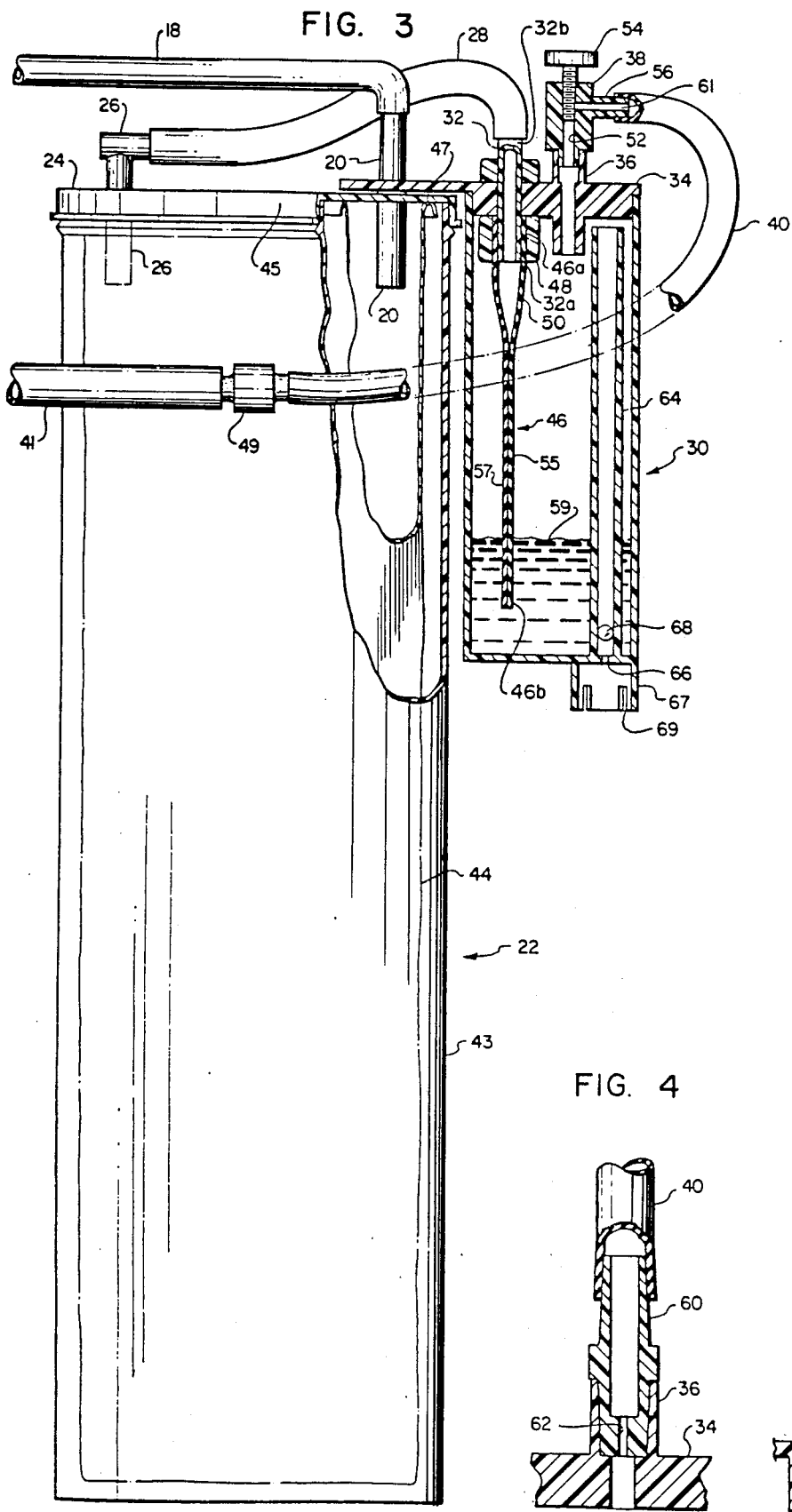

SUCTION DRAINAGE APPARATUS

This is a continuation, of application Ser. No. 434,681, filed Oct. 15, 1982, now abandoned.

BACKGROUND OF THE INVENTION

1. Field of the Invention

The present invention relates to drainage of fluids from body cavities and, more particularly, to an apparatus for use in draining fluids from the chest cavity.

2. The Prior Art

The thoracic or chest cavity is a closed structure essentially formed by the thoracic skeleton and muscles. The interior of the thoracic cavity is partitioned by the mediastinum, which consists of connective tissue which surrounds and holds together the esophagus, trachea, heart, aorta and other major vessels. The mediastinum divides the interior of the thoracic cavity into lung chambers (called pleural cavities), each of which contains one of the lungs.

The lungs are composed of elastic fibers which expand and contract during the normal breathing process. Expansion of the lung occurs during inhalation. When a person inhales, the diaphragm, which is mostly muscle, contracts and pulls downward. At the same time the chest muscles pull the chest wall up and out, with the result that the two chambers inside the thoracic cavity are expanded. The expansion of the two chambers in the thoracic cavity creates a negative pressure which exerts a pull on the lungs causing the lungs to expand and thereby allowing air to be drawn into the lungs. Similarly, during exhalation the rib cage and diaphragm contract, reducing the negative pressure in the two chambers which reduces the force on the lungs allowing them to contract so that sir is exhaled.

When the chest wall is penetrated, either by surgical intervention or accidentally, air is permitted to enter the pleural cavity. As air enters negative pressure is no longer exerted on the lung, which results in pneumothorax, a condition in which the elastic fibers of the lung recoil or collapse. If air continues to leak into the pleural cavity a condition known as tension pneumothorax may develop. In this condition the pressure within the pleural cavity rises to the point where it causes the mediastinum, including the heart and the other major vessels supported in the mediastinum, to be pushed towards the unaffected lung. Should the pressure become great enough it can collapse the unaffected lung and interfere with heart actinon and can thus lead to death within a few minutes.

In order to restore normal breathing following pneumothorax, the air and other fluids which have entered the pleural cavity must be removed from around the lung. This is typically accomplished by inserting one or more chest catheters into the pleural cavity and then connecting the catheters to a drainage system which is used to collect the fluids drained from the pleural cavity.

There are several types of prior art drainage systems which have been used for this purpose. For example, one type of system utilizes gravity to effect drainage of the fluids from the pleural cavity. In this type of system, a bottle is placed below the level of the patient's chest. The bottle is closed at its top by a rubber stopper through which a drainage tube is inserted. The drainage tube is attached at one end to the catheter inserted into the patient's chest. The other end of the drainage tube extends through the stopper to a point near the bottom of the bottle. A sterile liquid such as saline solution is used to fill the bottle to a point which covers the end of the drainage tube. The sterile liquid is intended to act as a seal or one-way check valve which prevents air from moving back up through the drainage tube to the patient's chest. The bottle is also vented to atmosphere through the rubber stopper so that when the bottle is placed below the level of the patient's chest, gravity will effect drainage of fluid from the pleural cavity into the drainage bottle.

This system will not work if the lung is fully collapsed, and it has the further disadvantage that it is difficult to overcome air leaks around the catheter. Moreover, at times there may be a major fluid leak which requires additional drainage capacity. Thus, suction drainage systems have also been used in the prior art to obtain increased drainage capacity. Suction drainage systems typically include a water manometer which is connected to a source of suction and which controls the level of suction applied to the pleural cavity of the patient, since an uncontrolled level of suction may damage the surrounding tissue. The manometer bottle is in turn connected to a bottle which contains a water seal similar to the type of water seal used in a gravity drainage system. The bottle containing the water seal may then be also connected to a third bottle which is used as the drainage bottle for collecting the fluids that are drained from the patient's chest cavity.

One of the disadvantages experienced with the use of this type of three bottle suction drainage system is the rather complicated procedure for setting up the system and interconnecting the three bottles. Also, the system is somewhat inconvenient to use because the bottles must be rinsed, washed and sterilized before they can be used again on other patients.

A more recent system which overcomes some of the disadvantages of the three bottle suction drainage system is illustrated and described in U.S. Pat. Nos. 3,363,626 and 3,363,627. These patents describe a unitary or consolidated "three bottle" apparatus which is constructed of plastic and which is disposable. Rather than using separate bottles, the apparatus replaces the bottles with separate chambers that are formed as part of a single container. The apparatus retains the basic concept of the three bottle suction drainage system because one of the chambers of the apparatus is used as a manometer, and is connected to a second chamber which is used as a water seal. The second chamber is connected to a third chamber which is used as the drainage chamber for receiving fluids drained from the patient's chest cavity.

While the apparatus described in these patents simplifies the set up procedure of the basic three bottle suction drainage system and provides for convenient disposal of the system after each use, this apparatus is relatively complicated in its structure and is expensive to manufacture and use. Moreover, like the gravity drainage system and the three bottle suction drainage system, the apparatus of these patents continues to rely upon the use of an underwater seal which is intended to prevent fluids from re-entering the patient's pleural cavity. However, in practice, an underwater seal does not always prevent fluids from re-entering the patient's chest cavity. For example, if the patient's bronchial tubes are blocked the patient must take deeper breaths in order to expand the lungs to permit air flow around this blockage. When the patient gasps for air or continually takes these kinds of deep breaths, a sufficiently high negative pressure may be developed in the pleural cavity that the liquid used to provide the water seal may be sucked back through the tube and catheter and into the pleural cavity. This obviously increases the risk of contamination to the patient, as well as hampering recovery of the patient's normal respiration.

Thus, what is needed in the art is a suction drainage system which is less expensive and can be economically disposed of after each use and which also overcomes the disadvantages of the prior art type of systems which require the use of an underwater seal, with its attendant disadvantages. Such an invention is described and claimed herein.

SUMMARY AND OBJECTS OF THE INVENTION

One important object of the present invention is to provide an apparatus for draining fluids from the body cavity of a patient which includes structure for effectively sealing the drainage system to prevent backflow of drained fluids but which seal is accomplished without the use of an underwater seal.

Another important object of the present invention is to provide an apparatus for draining fluids from a body cavity which is simple in its construction, compact, easy to handle and which can be economically disposed of after each use.

Yet another important object of the present invention is to provide an apparatus which combines in a simple and effective way the structure for accomplishing pressure regulation and sealing of a suction drainage system.

In accordance with these and other objects of the present invention, in one presently preferred embodiment a small, disposable suction control chamber contains a novel check valve and structure for regulating the amount of suction applied to the catheter and drainage tube inserted into the pleural cavity of a patient. The disposable suction control chamber may be removably mounted on a standard suction collection apparatus which is used for receiving the fluids drained from the pleural cavity. The check valve effectively prevents backflow of the drained fluids without the use of an underwater seal as in the prior art type suction drainage systems. The pressure regulating structure of the suction control chamber also eliminates the need for a water manometer and thus permits the suction collection chamber to be constructed in a very compact size so that it can be economically disposed of after each use.

BRIEF DESCRIPTION OF THE DRAWINGS

The foregoing and other features, advantages and objects of the present invention will become more fully apparent from the following detailed description of specific embodiments thereof, especially when taken in conjunction with the accompanying drawings, wherein:

FIG. 1 is a schematic illustration of the apparatus of the present invention connected to a patient to effect drainage of the chest cavity;

FIG. 2 is a perspective illustration of the suction drainage system of the present invention which illustrates the suction control chamber connected to a typical suction collection apparatus;

FIG. 2a is an enlarged perspective illustration in partial cross-section, illustrating a one-way valve that may be used to prevent loss of vacuum in the suction collection container;

FIG. 3 is a view in vertical section of the suction control chamber of the present invention, and also showing portions of the suction collection container in partial cross-section;

FIG. 4 is a view in vertical section of a flow restricter which can be substituted for the suction control valve shown in the apparatus in FIG. 3; and FIG. 5 is a view in vertical section which illustrates an enlarged view of the structure of the apparatus of the present invention which may be used in measuring the level of suction which is applied.

DETAILED DESCRIPTION OF THE PREFERRED EMBODIMENTS

Referring specifically to FIG. 1 of the accompanying drawings, a patient 10 is schematically illustrated with two drainage tubes 12, 14 connected in flow communication with his thoracic cavity. The number of tubes so used depends upon the nature of the procedure and is not a limiting feature of the present invention. The drainage tubes 12, 14 are connected to respective legs of a Y-connector 16 so as to feed a common flow tube 18 connected to the stem of the connector 16. Flow tube 18 is connected to a fitting 20 (see FIG. 2) which projects upwardly from the cover 24 of a suction collection container generally designated at 22, to form a first flow path 23. Also projecting through cover 24 is a second fitting 26 (see FIG. 2) to which a further flow tube 28 has one of its ends 28a connected. The other end 28b of tube 28 is connected to an inlet fitting 32 projecting upwardly from the top wall or cover 34 of a suction control chamber designated at 30. An outlet fitting 36 also projects upwardly from cover 34 and is connected to an adjustable control valve 38. Inlet fitting 32 and outlet fitting 36 are connected in series to form part of a second flow path 37 through which negative or suction pressure is adjustably applied to the interior of suction control chamber 30 by means of valve 38, which is connected by tubes 40 and 41 to a negative pressure or vacuum source (not shown).

The relatively small suction control chamber 30 can be mounted on the larger suction collection container 22 by means of the cover 34. The cover 34 (see FIG. 2) includes a horizontal projection 42 which engages fitting 20 through aperture 43. As hereinafter more fully described, suction applied to chamber 30 is transmitted to container 22 via tube 28. From container 22 the suction is applied to the chest cavity of patient 10 via tubes 18, 12 and 14. Liquid drawn through tubes 12, 14 and 18 is thus suctioned into and collected in container 22 while drained gases pass above the collected liquid, through tube 28 to chamber 30 where they are exhausted through tubes 40 and 41 by the vacuum source.

Referring more specifically to FIGS. 2 and 3, the suction collection container generally designated at 22 may be any suitable type of suction collection apparatus for effecting thoracic drainage, such as for example the apparatus illustrated and described in U.S. Pat. No. 3,719,197 which is incorporated herein by reference. Briefly described, the suction collection container 22 includes a rigid outer canister 43 that is cylindrical in shape, although the shape is not critical. The rigid outer canister 43 is enclosed at its top by a cover 24 which has a depending flange 45 for air-tight engagement over the upper open end of the canister 43. A plastic receiver or canister liner 44 depends from the cover 24 and is fused or otherwise secured to the underside of the cover 24 entirely around the upper periphery of the liner 44 as indicated at 47 (see FIG. 3). The cover 24 is preferably of a relatively rigid plastic material, while the liner or receiver 44 which depends from the cover 24 is preferably a flexible thermoplastic material. The securement of the upper end portion of the liner 44 to the cover 24 is completely air-tight and positive. The liner receiver 44 is therefore completely sealed except for fittings 20 and 26, which may conveniently be molded as part of the cover 24 and which project from the cover 24 into the interior of the liner receiver 44.

The outer canister 43 has a T fitting 49 (See also FIG. 2a) secured to nipple 51 in the wall of the canister 43. As shown best in FIGS. 2 and 2a, one arm of the T fitting 49 is connected by tube 40 to the outlet fitting 36 of the control valve 38 on the suction control chamber 30. The other arm of the T fitting 49 is connected to the tubing 41 connected to the source of suction (not shown) used to effect drainage of the patient's chest cavity. A resilient, one-way flutter valve 53 is attached at the nipple 51 and is enclosed by the collar portion 70 of T fitting 49. If suction through tube 41 is terminated, a positive pressure is established across valve 53 from its outlet end 53a to its inlet end 53b, which serves to help seal valve 53. Valve 53 thus prevents the loss of vacuum from the inside of canister 43 and subsequent collapse of the liner 44 if the source of vacuum is disconnected for any reason.

The vacuum or negative pressure applied through tube 41 is communicated through the collar portion 70 of T fitting 49 and through valve 53 to the interior of the rigid canister 43. As described in the aforementioned patent, in this manner negative pressure or vacuum created inside the interior of the receiver or liner 44 is countervailed by the vacuum that is established inside of the canister 43 but outside the liner 44, thus preventing collapsing of the liner receiver 44 during the time that the vacuum is applied.

Advantageously, since the liner receiver 44 is heat sealed or othewise secured to the cover 24 once the liner has been completely filled with the fluids drained from the patient's chest cavity, the cover 24 and liner receiver 44 may simply be removed and disposed of intact. This eliminates the need for having to wash and resterilize the suction collection container 22 and also eliminates additional risk of contamination to nurses and other hospital staff.

The specific structure and operation of the presently preferred embodiment of the suction control chamber 30 of the present invention is best illustrated and described with reference to FIG. 3. Inlet fitting 32 extends through the cover 34 of chamber 30 and has its interior end engaged within one end of an elastomeric duck-bill member generally designated at 46. Duck-bill member 46 is a radially flattened, elongated elastomeric tube which, in its unflexed state, prevents axial flow therethrough because its opposed flattened surfaces 55, 57 abut one another. The ingress end 46a of member 46 is stretched over the interior end 32a of fitting 32 and may be annularly clamped thereto by a clamping ring 48, or bonded directly to fitting 32. The inlet opening 32b of fitting 32 thus communicates with the interior of the resiliently expanded portion 50 of the member 46. Member 46 can be made of any elastomeric material and, in the preferred embodiment, is made of natural rubber. Clamping ring 48 is made of latex or other similar material suitable for clamping the ingress end 46a of member 46 about fitting 32.

Outlet fitting 36 is secured to the external side of cover 34 to valve 38 by means of a friction fit or the like. Valve 38 may be any suitable metering valve and, in the preferred embodiment, includes a threaded interior bore 52. A screw 54 threadingly engages bore 52. An outlet fitting 56 is adapted to be connected to tube 40 and has a throughbore 61 that communicates with the interior bore 52. By adjusting the depth of screw 54 in bore 52, the flow restriction between fittings 56 and 36 can be varied so as to adjust the suction or negative pressure applied to the interior of suction control chamber 30.

Alternatively, as illustrated in FIG. 4, the valve 38 may be replaced by a flow restrictor 60 which is adapted to engage fitting 36 in a friction fit, or which may be bonded thereto. Flow restrictor 60 has a flow path which includes a narrowed portion 62 which restricts gaseous flow and thereby limits the suction pressure applied to chamber 30.

In practice, it has been found that the size of the restriction provided by bore 62 (see FIG. 4) or screw 54 (see FIG. 3) should be designed so that gaseous flow through the restriction will be maintained at sonic velocity over a range of absolute line pressures in tube 40 from approximately zero to one-half an atmosphere. For example, in one presently preferred embodiment, the restrictor 62 is sized at 0.0465 in., which causes a constant flow rate which in combination with aperture 66 results in an essentially constant negative pressure of about 20 cm of water using typical hospital vacuum wall outlets or portable vacuum pumps. This level of suction can be safely applied to the pleural cavity without damaging surrounding tissue.

With continued reference to FIG. 3, the pressure within suction control chamber 30 is monitored by means of a pressure monitoring tube 64. Tube 64 preferably has gradations (not shown) spaced longitudinally along its exterior and calibrated in units of pressure. The tube 64 is oriented vertically within suction control chamber 30 and has its lower end communicating with the ambient pressure outside of chamber 30 by means of a small aperture 66 located in the bottom wall of the chamber 30. Aperture 66 is sized so that it is slightly larger than the flow restriction provided by screw 54 or restrictor tube 60. Using the example noted above wherein restrictor 62 is 0.0465 in., a suitable size for aperture 66 would be 0.078 in.

In the preferred embodiment the tube 64 is molded integrally with the bottom wall of chamber 30, with the lower end of the tube disposed concentrically about aperture 66. A round projection 67 having one or more slots 69 is formed on the bottom of chamber 30 and surrounds the aperture 66. The projection 67 prevents occlusion of the aperture 66 by a finger or by other objects.

A ball 68 or other relatively light-weight pressure responsive indicator is disposed within tube 64, which has its upper end open to the interior of chamber 30. Ball 68 is typically made of polypropylene or similar material. When the pressure in chamber 30 is reduced by the applied suction to a lever below ambient pressure, air rushes in through aperture 66 causing ball 68 to rise in tube 64. The level attained by the ball corresponds to the magnitude of the pressure differential across tube 64 and hence, reflects the pressure level within chamber 30. The calibrated gradations (not shown) on tube 64 provide a reading of that pressure as a function of the height attained by the ball within tapered tube 64.

When negative pressure is introduced into the suction control chamber 30 through valve 38, a positive pressure differential is developed across duck-bill member 46 from its upper ingress end 46a to its lower egress end 46b. Gas drawn through fitting 32, which is suctioned from the patient's chest cavity via tube 28, collection container 22 and and tube 18, forces a radial expansion of member 46 to permit flow therethrough. This gas is then evacuated from chamber 30 via fitting 36. If the pressure in chamber 30 should exceed the pressure in liner 44, a negative pressure differential is created between upper ingress end 46a and lower egress end 46b. Duck-bill member 46 is thereby radially compressed, rendering the seal against backflow to liner 44 even stronger than that provided by the natural resilience of member 46. It will therefore be appreciated that member 46 serves as mechanical check valve which eliminates the need for a water seal.

However, for many applications it may be desirable to till chamber 30 with a sterile saline solution or other sterile liquid 59 up to a level which is above the egress end 46b of duck bill member 46 (a check valve), as illustrated in FIGS. 2 and 3. The liquid 59 is not provided to effect a seal but it permits drained gases to be visually observed as they bubble through the liquid 59. In the absence of such a liquid, the gases will be efficiently drained from the pleural cavity without danger of backflow; however, there would be no visible indication of such gaseous fluid drainage. In addition, the liquid 59 provides a means of permitting detection of leaks in the system between the patient and the check valve 46. Such a leak would be easily detected by the excessive bubbling from the egress end of member 46 through the liquid 59. Importantly, however, the liquid 59 cannot be suctioned back into the liner 44 or patient's cavity because of the presence of the mechanical check valve provided by duck bill member 46.

In order to provide an example of the size of the suction control chamber and its components, a set of dimensional values is provided hereinbelow. It must be stressed, however, that the dimensions are by way of example only and are not to be construed as limiting the scope of the invention. In this example, chamber 30 is a transparent plastic cylinder having an inside diameter of 1.690 inches, an outside diameter of 1.750 inches, and an axial length of 4.425 inches. The base of the chamber is preferably formed integrally with the cylinder and has an axial depth of 0.150 inches. Pressure monitoring tube 64 (see FIG. 5) is preferably formed integrally with the chamber base and has an axial length of 4.000 inches. The outer diameter of tube 64 is 0.410 inch and the inner diameter tapers from 0.250 inch at its lower end to 0.350 inch at its upper end. Duck bill member 46 is 4.000 inches long, 0.800 inch wide and 0.062 inch thick. A typical range of pressure calibration of tube 64 is between zero to twenty centimeters of water.

The invention may be embodied in other specific forms without departing from its spirit or essential characteristics. The described embodiment is to be considered in all respects only as illustrative and not restrictive and the scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A suction drainage system for draining liquid and gaseous fluids from a body cavity, said system comprising:
    means for collecting liquid and gaseous fluids from a body cavity;
    means for establishing a first flow path between a body cavity and said means for collecting fluids;
    means for establishing a second flow path between said means for collecting fluids and a source of vacuum;
    means, disposed in said second flow path, for providing one-way flow of fluid from said means for collecting fluids to a suction control chamber; and
    a suction control chamber having:
    inlet and outlet openings connected in series in said second flow path;
        said means for providing one-way flow disposed within said suction control chamber in series with said inlet opening;
        a flow restrictor in fluid communication with said outlet opening, said flow restrictor sized so that gaseous flow through said flow restrictor is maintained at sonic velocity over a range of absolute pressure from zero to one half of an atmosphere;
        a sterile liquid disposed in said suction control chamber for providing an indication of the discharge of gaseous fluids from said one-way flow means; and
        means for venting said suction control chamber to ambient pressure.

2. The suction drainage system according to claim 1 wherein said means for providing one-way flow comprise an elastomeric member having an inlet and an outlet, and having two normally abutting opposed surfaces which are separable in response to an application of a positive differential pressure established said elastomeric member from its inlet to its outlet.

3. The suction drainage system according to claim 1 wherein said suction control chamber includes means for removably attaching said suction control chamber to said means for collecting said drained fluids.

4. The suction drainage system according to claim 1 wherein said flow restrictor is adjustable.

5. The suction drainage system according to claim 4 wherein said adjustable flow restrictor includes a threaded bore and a screw which engages said threaded bore.

6. The suction drainage system according to claim 1 wherein said flow restrictor is an orifice.

7. The suction drainage system according to claim 1 wherein said means for venting the suction control chamber is sized slightly larger than said flow restrictor, whereby said flow restrictor and said means for venting the suction control chamber will provide in combination an essentially constant level of negative pressure inside said suction control chamber.

8. A suction drainage system for draining liquid and gaseous fluids from a body cavity, said system comprising:
    means for collecting liquid and gaseous fluids from a body cavity;
    means for establishing a first flow path between a body cavity and said means for collecting fluids;

means for establishing a second flow path between said means for collecting fluids and a source of vacuum;

means disposed in said second flow path for providing one-way flow of fluid from said means for collecting fluids to a suction control chamber; and a suction control chamber having:

inlet and outlet openings connected in series in said second flow path;

said means for providing one-way flow disposed within said suction control chamber in series with said inlet opening;

a flow restrictor in fluid communication with said outlet opening;

a sterile liquid disposed in said suction control chamber for providing an indication of the discharge of gaseous fluids from said one-way flow means;

means for venting said suction control chamber to ambient pressure; and pressure monitoring means for providing an indication of the pressure in said suction control chamber, said pressure monitoring means including a hollow tapered tube having first and second ends, said first end having an aperture with communicates with ambient pressure external to said suction control chamber, said second end being open and disposed within said suction control chamber and a movable, pressure responsive indicator disposed in said tube for assuming a position between said first and second tube ends which is proportional to the differential between said ambient pressure and the pressure within said suction control chamber.

9. The suction drainage system according to claim 8 wherein said means for providing one-way flow comprises an elastomeric member having an inlet and an outlet, and having two normally abutting opposed surfaces which are separable in response to application of a positive differential pressure established across said elastomeric member from its inlet to its outlet.

10. The suction drainage system according to claim 8 wherein said flow restrictor is an adjustable valve means.

11. The suction drainage system according to claim 10 wherein said adjustable valve means includes a threaded bore and a screw which engages said threaded bore.

12. The suction drainage system according to claim 8 wherein said flow restrictor is an orifice.

13. The suction drainage system according to claim 12 wherein said orifice is sized so that gaseous flow through said orifice is maintained at sonic velocity over a range of absolute pressure from zero to one-half an atmosphere.

14. The suction drainage system according to claim 8 wherein said suction control chamber comprises means for removable attaching said suction control chamber to said means for collecting said drained fluids.

15. The suction drainage system according to claim 8 further including means for precluding said aperture from being occluded by a finger or other like object.

16. The suction drainage system according to claim 8 wherein said pressure responsive indicator is a ball constructed and arranged to move in said tube responsive to said pressure differential.

17. The suction drainage system according to claim 8 wherein said means for venting said suction control chamber is sized slightly greater than said flow restrictor, whereby said flow restrictor and said means for venting said suction control chamber will provide in combination an essentially constant level of negative pressure inside said suction control chamber.

18. A suction drainage system for draining liquid and gaseous fluids from a body cavity, said system comprising:

means for collecting liquid and gaseous fluids from a body cavity, said means having:

a rigid outer canister;

a disposable liner receiver inside of said canister, said liner having a cover; and means for communicating negative pressure to both the inside of said liner receiver and to the inside of said canister so as to maintain the liner receiver expanded when vacuum is applied to the system;

means for establishing a first flow path between a body cavity and said means for collecting fluids;

means for establishing a second flow path between said means for collecting fluids and a source of vacuum;

means disposed in said second flow path for providing one-way flow of fluid from said means for collecting fluids to a suction control chamber;

a suction control chamber having:

inlet and outlet openings connected in series in said second flow path;

said means for providing one-way flow disposed within said suction control chamber is series with said inlet opening;

a flow restrictor in fluid communication with said outlet opening; and means for venting said suction control chamber to ambient pressure; and a one-way valve disposed downstream from said means for communicating said negative pressure to the inside of said canister, thereby preventing the loss of vacuum within said canister upon termination of suction from said vacuum source.

19. The suction drainage system according to claim 18 wherein said means for providing one-way flow comprise an elastomeric member having an inlet and an outlet, and having two normally abutting opposed surface which are separable in response to an application of a positive differential pressure established across said elastomeric member from its inlet to its outlet.

20. The suction drainage system according to claim 18 wherein said flow restrictor is an adjustable valve means.

21. The suction drainage system according to claim 20 wherein said adjustable valve means includes a threaded bore and a screw which engages said threaded bore.

22. The suction drainage system according to claim 18 wherein said flow restrictor is an orifice.

23. The suction drainage system according to claim 22 wherein said orifice is sized so that gaseous flow through said orifice is maintained at sonic velocity over a range of absolute pressure from zero to one-half an atmosphere.

24. The suction drainage system according to claim 18 wherein said suction control chamber comprises means for removably attaching said suction control chamber to said means for collecting said drained fluids.

25. The suction drainage system according to claim 18 wherein said means for venting said suction control chamber is sized slightly greater than said flow restrictor, whereby said flow restrictor and said means for venting said suction control chamber will provide in combination an essentially constant level of negative pressure inside said suction control chamber.

26. A suction drainage system for draining liquid and gaseous fluids from a body cavity, comprising:
means for collecting liquid and gaseous fluids from a body cavity, the means having:
a rigid outer canister;
a disposable liner receiver inside of the canister, the liner having a cover; and
means for communicating negative pressure to both the inside of the liner receiver and to the inside of the canister so as to maintain the liner receiver expanded when vacuum is applied to the system;
means for establishing a first flow path between a body cavity and the means for collecting fluids;
means for establishing a second flow path between the
means for collecting fluids and a source of vacuum;
means disposed in the second flow path for providing one-way flow of fluid from the means for collecting fluids to a suction control chamber; and
a suction control chamber having:
inlet and outlet openings connected in series in the second flow path;
the means for providing one-way flow disposed within said suction control chamber in series with said inlet opening;
a flow restrictor in fluid communication with said outlet opening;
a sterile liquid disposed in said suction control chamber for providing an indication of the discharge of gaseous fluids from said one-way flow means; and
means for venting said suction control chamber to ambient pressure.

27. A suction control chamber for use in applying suction to a body cavity through a suction collection container, said suction control chamber comprising:
an inlet and outlet, said inlet being adapted to be connection in fluid flow communication with said collection container, said outlet being adapted to be connected in fluid flow communicationn with a source of suction;
check valve means disposed at the inlet of said suction control chamber to permit one-way flow of fluids from said inlet into said suction control chamber;
means for establishing an essentially constant level of negative pressure inside said suction control chamber, said means further including a flow restrictor in fluid communication with said outlet of said suction control chamber, said flow restrictor being sized so that gaseous flow through said flow restrictor is maintained at sonic velocity over a range of absolute pressure from zero to one-half an atmosphere;
means for venting said suction control chamber to ambient pressure, said means for venting being sized slightly greater than said flow restrictor;
a sterile liquid disposed inside said suction control chamber for providing an indication that gaseous fluids from said check valve means are being discharged through said sterile liquid; and
pressure monitoring means disposed in said suction control chamber for providing an indication of the pressure therein.

28. The suction control chamber according to claim 27 further including means for removably mounting said suction control chamber on said collection container.

29. The suction control chamber according to claim 27 wherein said check valve means is an elastomeric member having two normally abutting opposed surfaces which are separable in response to a positive pressure differential established across said check valve means.

30. The suction control chamber according to claim 27 wherein said pressure monitoring means includes:
a hollow tapered tube having first and second ends, said first end having an aperture which communicates with ambient pressure external to said suction control chamber, said second end being open and disposed within said suction control chamber; and
a movable, pressure responsive indicator disposed in said tube for assuming a position between said first and second tube ends which is proportional to the differential between said ambient pressure and the pressure within said suction control chamber.

31. The suction control chamber according to claim 30 further including means for precluding said aperture from being occluded by a finger or other object.

32. The suction control chamber according to claim 30 wherein said pressure responsive indicator is a ball constructed and arranged to move in said tube responsible to said pressure differential.

* * * * *